United States Patent [19]

Naujoks et al.

[11] Patent Number: 4,939,082
[45] Date of Patent: Jul. 3, 1990

[54] PROCESS AND MONOCLONAL ANTIBODY FOR THE SPECIFIC DETERMINATION OF PANCREAS ALPHA-AMYLASE IN THE PRESENCE OF SALIVA ALPHA-AMYLASE

[75] Inventors: Kurt W. Naujoks, Gauting; Willie Gerhardt, Helsingborg; Christa Hübner-Parajsz, Tutzing; Karl Wulff, Weilheim; Herbert Jungfer; Helmut Lenz, both of Tutzing; Winfried Albert, Pähl; August W. Wahlefeld, HohenpeiBenberg, all of Fed. Rep. of Germany

[73] Assignee: Boehringer Mannheim GmbH, Mannheim, Fed. Rep. of Germany

[21] Appl. No.: 326,885

[22] Filed: Mar. 21, 1989

Related U.S. Application Data

[63] Continuation of Ser. No. 673,855, Nov. 21, 1984, abandoned.

[30] Foreign Application Priority Data

Nov. 25, 1983 [DE] Fed. Rep. of Germany ....... 3342736

[51] Int. Cl.$^5$ ................. G01N 33/537; G01N 33/541; G01N 33/543; C12N 15/00
[52] U.S. Cl. ......................................... 435/7; 435/22; 435/70.21; 435/240.27; 435/172.2; 436/518; 436/548; 436/824; 436/828; 530/387; 530/808; 530/809; 935/106; 935/110
[58] Field of Search ................... 435/7, 22, 68, 240.27, 435/172.2; 436/518, 548, 824, 828; 530/387, 808, 809; 935/106, 108, 110

[56] References Cited

U.S. PATENT DOCUMENTS

| | | | |
|---|---|---|---|
| 4,012,285 | 3/1977 | Pfleideier et al. | 435/7 X |
| 4,474,892 | 10/1984 | Murad et al. | 436/808 X |
| 4,863,728 | 9/1989 | Gerber et al. | 530/387 X |

FOREIGN PATENT DOCUMENTS 58-183098 10/1983 Japan .

OTHER PUBLICATIONS

Goding, J. W., Journal of Immunological Methods, 1980, vol. 39, pp. 285–308.
Mishell et al., Selected Methods In Cellular Immunology, W. H. Freeman and Co., San Francisco, 1980, pp. 43–54.
Whitlow et al., Clin. Chem., vol. 25, No. 3, 1979, pp. 481–483.
Hagele et al., Clin. Chem., vol. 28, No. 11, 1982, pp. 2201–2205.

Primary Examiner—David M. Naff
Attorney, Agent, or Firm—Felfe & Lynch

[57] ABSTRACT

In body fluids containing saliva alpha amylase and pancreatic alpha amylase, pancreatic alpha amylase is determined with a monoclonal antibody which specifically binds but does not inhibit saliva alpha amylase and which has a cross-reactivity of 5% or less toward pancreatic alpha amylase. The monoclonal antibody binds salvia alpha amylase to form a complex which is separated to permit determining pancreatic alpha amylase with an amylase detection system. The complex may be separated by precipitating with a precipitating agent such as an anti-antibody or protein A, or by immobilizing the monoclonal antibody on a solid carrier. The monoclonal antibody is preferably produced by immunizing a host animal with an immunogen containing aluminum hydroxide, *Bordatella pertussis* and native saliva alpha amylase at least 7 times over a period of at least 9 months, fusing B lymphocytes of the immunized host animal with a transforming agent to produce hybridomas, cloning and culturing the hybridomas, and screening antibodies formed.

24 Claims, No Drawings

PROCESS AND MONOCLONAL ANTIBODY FOR THE SPECIFIC DETERMINATION OF PANCREAS ALPHA-AMYLASE IN THE PRESENCE OF SALIVA ALPHA-AMYLASE

This application is a continuation of Ser. No. 673,855, filed Nov. 21, 1984, now abandoned.

The present invention is concerned with a process and reagent for the specific determination of pancreas α-amylase in the presence of saliva α-amylase.

α-Amylase (E.C. 3.2.1.1) breaks down 1,4-d-glucosidically linked oligo- and polysaccharide preponderantly by the random hydrolysis of the 1,4-α-glycosidic bonds to give maltose and malto-oligosaccharides. Besides industrial fermentation technology, the enzyme is of considerable importance in clinical analysis and diagnosis. Thus, in the case of numerous diseases, the α-amylase content in the body fluids, such as serum, urine and duodenal secreta, changes considerably.

However, in the body, there occur substantially two α-amylase enyzmes, the pancreas enzyme and the saliva enzyme. Since diagnostic importance is only associated with the pancreas enzyme, the problem exists of analytically differentiating these two α-amylases (in the presence of further isoenzymes which occur rarely and only in small amounts). The difficulty is that the two multiple forms have a similar structure and are immunologically identical (K. Lorentz, Laboratorinumsblätter 32, 118/1982).

For the elimination of the activity of the saliva enzyme, it is known to use adsorption on anion exchangers, inhibition by a wheat protein or electrophoresis or electrofocussing. However, these processes are either unsatisfactory in their separation action or are too laborious for a routine diagnosis. Amongst the known methods, only the process described in Clin. Chem. 28(7), 1524–1527/1982 of inhibiting the enzyme of the saliva type by an inhibitor obtained from wheat germ involves an expenditure of time which is acceptable for routine diagnosis but the selectivity is unsatisfactory. Even in the case of optimum inhibitor concentration, about 13% of the activity of the saliva-type enzyme is maintained, whereas the activity of the pancreas enzyme is reduced to about 81%.

Therefore, it is an object of the present invention to overcome this disadvantage and to provide a process and a reagent which make possible a rapid, simple and dependable determination in body fluids of the pancreas α-amylase in the presence of α-amylase of the saliva type.

Thus, according to the present invention, there is provided a process for the specific determination of pancreas α-amylase in body fluids in the presence of saliva α-amylase, especially in serum, plasma, duodenal juice or urine, by reaction with a system for the detection of α-amylase in the presence of an inhibiting agent for saliva α-amylase, wherein, instead of an inhibiting agent, there is used a monoclonal antibody which specifically binds but does not inhibit saliva alpha amylase and which has a cross-reactivity of 5% or less towards pancreas α-amylase.

The process according to the present invention depends upon the very surprising discovery of a monoclonal antibody with a very low cross-reactivity towards the pancreas enzyme. This was not to have been expected since it was known that the saliva enzyme and the pancreas enzyme are immunologically identical (Gerhard Pfleiderer, Lab. Med, 7, 189–193; K. Lorentz, loc. cit.). Thus, Morton K. Schwarz, in "Immunoassay of Enzymes—an Overview", 1983, pages 4 to 9, states, for example, that antibodies against human saliva α-amylase inhibit the enzyme of the saliva type up to 78% and the pancreas enzyme up to 75%. Therefore, it could not have been foreseen that it would be possible to develop a process which would make possible a practically quantitative differentiation of the two enzymes on an immunological basis.

The hybridoma cell lines used for the inventive process are deposited with the National Collection of Animal Cell Cultures, Porton Down, England, under NCACC Nos. as follows: 84111305 (clone 79); 84111304 (clone 1A813E10); 84111303 (clone 1A814A 7); 84111302 (clone 32C516E3; 84111301 (clone 32C518F11). These clones were obtained by immunisation of experimental animals with native or modified saliva α-amylase, fusion of B-lymphocytes of the so obtained immunised animals with transforming agents, cloning and culturing of the so obtained hybrid cells which produce the monoclonal antibodies and isolation of the latter. Especially preferred animals for the preparation of the saliva α-amylase antibodies include rats and mice. The immunisation takes place either with native human saliva α-amylase or with modified saliva amylase. If native enzyme is used, then, for this purpose, there can be employed the commercially available, electrophoretically homogeneous preparations. Chemically modified saliva α-amylase can also be obtained by known methods of enzyme modification, such as are described, for example, in Federal Republic of Germany Patent Specification No. 25 43 994. Appropriate modification agents include, for example, N-bromosuccinimide (NBS), which oxidises tryptophane groups in the proteins (BBA, 143, 462–472/1967), carboxymethylation with iodoacetate (IAA), which mainly attacks histidine, or nitration with tetranitromethane (J. Biol. Chem. 238, 3307/1963), diazotisation with diazotised sulphanilic acid (Meth. Enzymol., 25, 515–531/1972), as well as reaction with dinitrofluorobenzene (DNFB) (J. Biol. Chem., 243, 5344–5353/1968). Apart from native enzyme, the enzyme modified with DNFB thereby proved to be the most appropriate.

Immunisation takes place by the conventional administration of native or modified enzyme, preferably in combination with adjuvant, the preferred adjuvant being aluminium hydroxide, together with *Bordatella pertussis*.

When native saliva α-amylase is used for the immunisation, then the immunisation preferably takes place over the course of at least 9 months with at least 7 immunisations (injections i.p.). If modified saliva α-amylase is used, than it is preferable to carry out a part of the immunisations in vitro. However, at least two immunisations in vivo are to take place before the in vitro immunisation is carried out. In the case of the latter, B-lymphocytes of the immunised animals are further cultured in a medium conditioned with thymocytes and antigens are added to the medium.

After immunisation has taken place, the B-lymphoctyes of the immunised animals are fused, according to the usual methods, with transforming agents. Examples of transforming agents which can be used in the scope of the present invention include myeloma cells, transforming viruses, for example Epstein-Barr virus, and the agents described in Federal Republic of Germany Patent Specification No. 32 45 665. Fusioning takes place according to the known process of Koehler and Milstein (Nature, 256, 495–497/1975). The hybrid cells hereby formed are cloned in the usual way, for example with the use of a commercially available cell sorter, and the clones obtained, which form the desired monoclonal antibodies, are cultured. On the basis of the cancer-like growth of the hybrid cells, these can be further cultured for an indefinite time and produce the desired monoclonal antibodies in any desired amount. With the so obtained monoclonal antibodies, the saliva α-amylase can be quantitatively absorbed from body fluids so that the remaining amylase activity is to be attributed to the pancreas α-amylase.

For the determination process according to the present invention, the monoclonal antibodies can be used as such or their corresponding fragments ($F_c$ fragments) displaying immunological properties. Thus, the term "monoclonal antibodies" is here also to be understood to include the fragments. Not only the complete antibodies but also their fragments can be used in immobilised form.

Surprisingly, the monoclonal antibodies used according to the present invention display towards the pancreas α-amylase a cross-reactivity of 5% or less and, in many cases, achieve a cross-reactivity of only 1%. Therefore, they can be used, instead of the previously known inhibiting material obtained from wheat germs, for the specific determination of pancreas α-amylase in body fluids.

The determination of the α-amylase as such takes place according to the methods known for this purpose. Since the monoclonal antibodies according to the present invention selectively bind the α-amylase of the saliva type and thus remove it from the enzyme activity determination, the values obtained in the case of the α-amylase determination in the presence of the monoclonal antibody correspond solely to the activity due to the pancreas enzyme.

The process according to the present invention is preferably carried out with a system for the detection of α-amylase which contains a maltopolyose with 4 to 7 glucose residues in the molecule, maltose phosphorylase, β-phosphoglucomutase, glucose-6-phosphate dehydrogenase and NAD.

A further system for the detection of α-amylase which is preferred according to the present invention contains nitrophenylmaltopolyose with 4 to 7 glucose residues in the molecule and α-glucosidase.

A further preferred detection system for α-amylase contains starch modified with determinable groups. The term modified starch includes, for example, starch which is modified with determinable groups, for example the commercial product "Phadebas" of Pharmazia, Sweden, as well as the product described in Federal Republic of Germany Patent Specification No. 28 12 154, and also starch changed by breakdown, for example carboxymethylstarch and torrefaction dextrins. All these systems are known and do not here require a more detailed description.

For the carrying out of the process according to the present invention, the sample liquid is mixed with the antibody according to the present invention, preferably in the form of a suspension, whereafter insolubles are separated off, preferably by brief centrifuging. The clear supernatant is then used in a conventional α-amylase test.

The monoclonal antibody present in the reagent according to the present invention can be not only in the complete form but also in the form of fragments and can also be fixed on a solid carrier, for example on immunosorptive paper or on the surface of synthetic resin test tubes or pipes. In this way, the α-amylase of the saliva type is bound on to the carrier, i.e. on to the solid phase, and in the liquid phase there can, therefore, be carried out, without further separation, the determination of the residual activity which is to be attributed to the pancreas enzyme.

Especially good results are obtained in the scope of the present invention when a monoclonal antibody preparation is employed which is obtained by mixing monoclonal antibodies produced by several different clones.

Since the complex formed from the monoclonal antibody and its antigen, the salvia α-amylase, is soluble, if the monoclonal antibody is not used in immobilised form, a further possibility for its separation is additionally to add a precipitating agent for the monoclonal antibody or for antibodies produced by the experimental animals in the case of the immunisation, an insoluble complex hereby being formed which contains saliva α-amylase, monoclonal antibody and precipitating agent.

The precipitating agent used is preferably an antibody against the monoclonal antibody or for the antibody (thus an anti-antibody) formed by the experimental animals in the case of the immunisation. A further possibility consists in the addition of protein A, preferably in immobilised form.

A preferred method of carrying out this embodiment of the process according to the present invention consists in that first there is formed a complex of monoclonal antibody and anti-antibody and the solution to be investigated is then added to this, which contains the α-amylases. Alternatively, however, there is first only added the monoclonal antibody and, after incubation for the formation of the antigen-antibody complex with the saliva α-amylase, there is then added the anti-antibody, with the formation of the insoluble complex.

For the embodiment of the process according to the present invention using an anti-antibody, there can be used, in principle, all anti-antibodies against the monoclonal antibody or the antibody formed by the experimental animals. In the case of the use of mice or rats for the production of the anti-saliva α-amylase serum, it is preferable to use anti-antibodies formed by sheep.

The present invention also provides a reagent for the specific determination of pancreas α-amylase in the presence of saliva α-amylase, in body fluids, especially in serum, duodenal juice, plasma or urine, containing a system for the detection of α-amylase and an inhibiting agent for saliva α-amylase, wherein, instead of an inhibiting agent, it contains a monoclonal antibody with a cross-reactivity of 5% or less towards pancreas α-amylase.

With regard to the system contained in the reagent according to the present invention for the detection of α-amylase and the other conditions, there apply correspondingly the above statements with regard to the process.

The present invention makes possible a simple and rapid determination of pancreas α-amylase, in the presence of α-amylase of the saliva type, in body fluids with high specificity and thus improves the possibilities of clinical diagnosis.

The following Examples are given for the purpose of illustrating the present invention:

EXAMPLE 1

(A) Balb/c mice are immunised with 100 μg. human saliva amylase in aluminium hydroxide with *Bordatella pertussis*. In an about eight-week rhythm, further immunisation is carried out three to four times, in each case with 50 μg. human saliva amylase in the same adjuvant. Four days before fusion, there is carried out a last intravenous immunisation with 50 μg. saliva amylase in physiological saline.

(B) The fusion of the spleen cells with Ag8.653 (ATDD CRL 1580) or SP2/0 (ATCC CRL 1581) myeloma cells is carried out according to the standard process according to J. of Imm. Meth., 39, 285–308. The fusion ratio of spleen to myeloma cells is 5:1. The fusion products are seeded on to 10 24-culture dishes (Costar) and fed with $5 \times 10^4$ peritoneal exudate cells per culture cup. Positive primary cultures (see Example 3) are, 3 to 4 weeks after fusion, cloned with the help of a fluorescence-activated cell sorter. The cells are placed individually in 96 Costar plates and fed with $2 \times 10^4$ peritoneal exudate cells.

EXAMPLE 2

Modification of the α-amylase with dinitrofluorobenzene

20 μmole salvia amylase/liter and 20 mMole dinitrofluorobenzene/liter (dissolved in a little ethanol) are mixed and incubated at ambient temperature for 10 minutes. The solution is then dialysed for 20 hours against phosphate buffer (50 mMole/liter; pH 6.8) (cold room). In the difference spectrum, the dialysate then shows an extinction increase of 0.070 at the wavelength 360 nm. Until used for immunisation, the solution is frozen. The protein concentration in the dialysate is 15 μmole/liter.

Mice are immunised, as in Example 1, with the modified α-amylase so obtained. The mice immunised with modified amylase all die after the second immunisation. Therefore, the spleen cells of these mice are cultured after the first boost and post-immunised according to the method of Luben (Molec. Immunology, 17, 635–639/1980) for four days in vitro in the presence of 100 μg. antigen in 30 ml. of medium. After 4 days, the cells are fusioned like the spleen cells obtained according to Example 1 and further treated.

EXAMPLE 3

In order to detect the concentration and specificity of amylase-binding antibodies in the serum of immunised mice or in the culture supernatant of the hybrid cells or in ascites, there is used an ELISA test principle. For this purpose, 96 ELISA plates (NUNC) are coated with sheep anti-mouse Fc antibodies. For the reduction of non-specific binding, the plates are post-coated with bovine serum albumin (2% in physiological saline). Thereafter, there is carried out an incubation with the sample containing the antibodies or with various dilutions thereof.

The subsequent incubation is carried out either with saliva amylase-peroxidase (POD) conjugate or with pancreas amylase-POD conjugate. The activity of the bound POD is determined with ABTS (2,2'-azinodi-[3-ethylbenzthiazoline-6-sulphonate]) (pH 4.4) and the extinction taken directly as a measure of the bound mouse antibody. For the determination of the cross-reaction, for each sample there is separately determined the binding of saliva- and pancreas amylase-POD and the extinction obtained with saliva amylase-POD taken as 100% binding. The simultaneously obtained extinction with pancreas-amylase-POD gives, in percentage of the extinction of the saliva amylase-POD, the cross-reaction of the sample.

4Clones were found in which no binding at all of the pancreas α-amylase-POD took place and 5 clones with cross-reactions of between 1.5 and below 5%. The clones separated out after the screening are expanded.

RPMI medium is described in J.A.M.A., 199, 519/1957 and is commercially available.

EXAMPLE 4

Immobilisation of the monoclonal antibody (MAB) by sheep anti-mouse AB and subsequent binding of the saliva amylase Ascites from mouse
sheep anti-mouse-AB (LgGFcγ): 19 g./liter
phosphate buffer, pH=7.0; 0.05 mole/liter
phosphate buffer, pH=7.0; 0.05 mole/liter with 2% bovine serum albumin
human saliva amylase: 1000 U/liter (μmole substrate reaction/ml./min. (37° C.) with 4-nitrophenylmaltoheptaoside as substrate)
human pancreas amylase: 1000 U/liter
acetic acid: 0.5 mole/liter
dipotassium hydrogen phosphate solution: 2 mole/liter.

The MAB from ascites is mixed in the ratio of 1:100 with sheep anti-mouse antibody. This mixture is diluted 1:2 with phosphate buffer and shaken for 15 minutes at 37° C. The resultant precipitate is washed twice with buffer and then dissolved in acetic acid (about 1/5 of the starting volume). After 5 minutes shaking, dipotassium hydrogen phosphate solution is added in a ratio of 1:2. The precipitate forms again. This is washed twice with phosphate buffer containing BSA (bovine serum albumin) and thereafter twice with buffer only. Subsequently, the precipitate is suspended in 1/5 of the starting volume with buffer. 50 μl. of the precipitate are applied to 50 μl. of saliva or pancreas amylase and incubated for 15 minutes at ambient temperature. Thereafter, the precipitate is centrifuged off and the supernatant further worked up according to Example 7. As control, there is used an amylase sample which is treated with 50 μl. of buffer instead of with preciptate.

EXAMPLE 5

Binding of the MAB on to saliva amylase and subsequent precipitation with sheep anti-mouse antibody The ascites with monoclonal antibodies is diluted with buffer in the ratio of 1:50. 50 μl. of this solution are shaken with 50 μl. saliva or pancreas amylase for 15 minutes at ambient temperature. As control, there is used, on the one hand, a mixture of ascites dilution with buffer (blank of the ascites) and, on the other hand, a mixture of amylase and buffer (control of the amylase activity). Subsequently, 50 μl. of the precipitating antiantibody are added thereto. After 10 minutes at ambient temperature, the precipitate is centrifuged off and the supernatant further worked up according to Example 7.

EXAMPLE 6

Immobilisation of the MAB by sheep anti-mouse antibodies and subsequent binding of human saliva amylase from a mixture of saliva and pancreas amylase Corresponding to Example 5, a mixture of human pancreas and saliva amylase (1000 U/liter of each) is incubated with pretreated precipitate. After centrifuging, the supernatant is further worked up according to Example 7.

EXAMPLE 7

Determination of remaining pancreas amylase

50 μl. of supernatant according to one of Examples 4 to 6 are added to 1 ml. of commercially available reagent for the determination of α-amylase with 4-nitrophenylmaltoheptaoside as substrate (Boehringer Mannheim, Cat. Order No. 568589). The activity of the supernatant is determined after carrying out at 37° C. The residual activities are determined as percentage activity, referred, in each case, to the concurrent controls. The residual activity in the case of Example 4 is 0 to 5% with saliva amylase and 70 to 95% with pancreas amylase. The experiment according to Example 5 gives residual activities with saliva amylase of 0 to 5% and with pancreas amylase of 80 to 95%. The simultaneous presence of both enzymes (Example 6) makes possible the selective precipitation of the saliva amylase, the pancreas amylase thereby remaining active and being determined to an extent of 80 to 95%.

It will be understood that the specification and examples are illustrative but not limitative of the present invention and that other embodiments within the spirit and scope of the invention will suggest themselves to those skilled in the art.

We claim:

1. Method for determining pancreatic alpha amylase in a body fluid sample which also contains salivary alpha amylase comprising contacting said body fluid sample with a monoclonal antibody which specifically binds to but does not inhibit salivary alpha amylase and has cross reactivity with pancreatic alpha amylase of 5% or less under conditions favoring formation of a complex of said monoclonal antibody and said salivary alpha amylase which removes said salivary alpha amylase from said fluid, adding a system for detection of alpha amylase to said body fluid sample and determining reaction of said system with pancreatic alpha amylase.

2. Method for determining pancreatic alpha amylase in a body fluid sample which also contains salivary alpha amylase comprising contacting said body fluid sample with a monoclonal antibody which specifically binds to but does not inhibit salivary alpha amylase and has cross reactivity of 5% or less with to praceatic alpha amylase under conditions favoring formation of a complex between said monoclonal antibody and salivary alpha amylse, adding a precipitating agent which precipitates said complex from said body fluid sample, separating precipitated complex from said body fluid sample, adding a system for detection of alpha amylase to said body fluid sample and determining reaction of said system and pancreatic alpha amylase.

3. Method of claim 2, wherein said precipitating agent is an anti-antibody for said monoclonal antibody.

4. Method of claim 2, wherein said precipitating agent is protein A.

5. Method of claim 3, wherein said anti-antibody is a sheep antibody.

6. Method of claim 1 or 2, wherein said system is a reagent containing a maltopolyose having from 4 to 7 glucose residues, maltose phosphorylase, β-phosphoglucomutase, glucose-6-phosphate dehydrogenase, and NAD.

7. Method of claim 1 or 2, wherein said system is a reagent containing a nitrophenylmaltopolyose having from 4 to 7 glucose residues and α-glucosidase.

8. Method of claim 1 or 2, wherein said system is a reagent containing starch modified by a determinable group.

9. Method of claim 1 or 2, wherein said monoclonal antibody is an antibody produced by immunizing a host animal with an immunogen containing aluminum hydroxide, *Bordatella pertussis* and native salivary alpha amylase at least seven times over a period of at least 9 months, fusing B lymphocytes of said immunized host animal with a transforming agent to produce hybridomas, cloning and culturing said hybridomas and screening antibodies formed by said hybridomas.

10. Method of claim 1 or 2 wherein said monoclonal antibody is selected from the group consisting of monoclonal antibody produced by hybridoma cell line NCACC 84111305, NCACC 84111304, NCACC 84111303, NCACCC 84111302, and NCACC 84111301.

11. Reagent useful in determining pancreatic alpha amylase in a body fluid sample comprising an immobilized monoclonal antibody which specifically binds to but does not inhibit salivary alpha amylase and has cross reactivity of 5% or less with pancreatic alpha amylase, and a system for detection of alpha amylase.

12. Reagent useful in determining pancreatic alpha amylase in a body fluid sample comprising a monoclonal antibody which specifically binds to but does not inhibit salivary alpha amylase and has cross reactivity of 5% or less with pancreatic alpha amylase, a precipitating agent which reacts with complex of said monoclonal antibody and salivary alpha amylase and a system for detection of alpha amylase.

13. Reagent of claim 11 or 12, wherein said system for detection of alpha amylase comprises a maltopolyose having from 4 to 7 glucose residues, maltose phosphorylase, β-phosphoglucomutase, glucose-6-phosphate dehydrogenase, and NAD.

14. Reagent of claim 11 or 12 wherein said system for detection of alpha amylase comprises a nitrophenylmaltopolyose having from 4 to 7 glucose residues and α-glucosidase.

15. Reagent of claim 11 or 12, wherein said system for detection of alpha amylase comprises a starch modified by a determinable group.

16. Reagent of claim 11 or 12, wherein said monoclonal antibody is an antibody produced by immunizing a host animal with an immunogen containing aluminum hydroxide, *Bordatella pertussis* and native salivary alpha amylase at least seven times over a period of at least 9 months, fusing B lymphocytes of said immunized host animal with a transforming agent to produce hybridomas, cloning and culturing siad hybridomas and screening antibodies formed by said hybridomas.

17. Reagent of claim 11 or 12, wherein said monoclonal antibody is selected from the group consisting of monoclonal antibody produced by hybridoma cell line NCACC 84111305, NCACC 84111304, NCACC 84111303, NCACCC 84111302, and NCACC 84111301.

18. Reagent of claim 12, wherein said precipitating agent is an anti-antibody for said monoclonal antibody.

19. Reagent of claim 12, wherein said precipitating agent is protein A.

20. Reagent of claim 18, wherein said anti-antibody is a sheep antibody.

21. Process for obtaining a monoclonal antibody which specifically binds to but does not inhibit salivary alpha amylase and has cross reactivity of 5% or less with pancreatic alpha amylase comprising immunizing a host animal with an immunogen containing native salivary alpha amylase, aluminum hydroxide and *Bordatella pertussis* at least seven times and over a period of at least 9 months, separating B lymphocytes from said host animal, fusing said B lymphocytes with a transforming agent to form hybridomas, and cloning said hybridomas under conditions favoring production of said monoclonal antibody.

22. Monoclonal antibody which specifically binds to but does not inhibit salivary alpha amylase and has cross reactivity of 5% or less with pancreatic alpha amylase.

23. Monoclonal antibody of claim 22, wherein said monoclonal antibody is of subclass IgG2bKappa.

24. Monoclonal antibody of claim 23, selected from the group consisting of monoclonal antibody produced by hybridoma cell line NCACC 84111305, NCACC 84111304, NCACC 84111303, NCACC 84111302, and NCACC 84111301.

* * * * *